US005173301A

United States Patent [19]

Itoh et al.

[11] Patent Number: 5,173,301

[45] Date of Patent: Dec. 22, 1992

[54] SURGICAL ADHESIVE

[75] Inventors: Tetsuo Itoh, Shiga; Takehisa Matsuda, Minoo, both of Japan

[73] Assignee: Sanyo Chemical Industries, Ltd., Kyoto, Japan

[21] Appl. No.: 799,322

[22] Filed: Nov. 27, 1991

[30] Foreign Application Priority Data

Nov. 27, 1990 [JP] Japan .................................. 2-327392

[51] Int. Cl.[5] ........................ A61F 13/02; C08G 18/38

[52] U.S. Cl. .................................... 424/448; 424/445; 523/118; 528/70; 528/904; 528/905

[58] Field of Search ................ 424/448, 445; 528/904, 528/905, 70; 523/118

[56] References Cited

U.S. PATENT DOCUMENTS

| | | | |
|---|---|---|---|
| 3,723,394 | 3/1973 | Gibier-Rambaud | 528/905 |
| 4,039,719 | 8/1977 | Masuda et al. | 428/339 |
| 4,403,083 | 9/1983 | Marans | 528/904 |
| 4,412,054 | 10/1983 | Yamabe | 528/904 |
| 4,740,534 | 4/1988 | Matsuda | 528/904 |
| 4,804,691 | 2/1989 | English | 528/905 |
| 4,994,542 | 2/1991 | Matsuda | 528/904 |
| 5,045,601 | 9/1991 | Capelli | 424/445 |

FOREIGN PATENT DOCUMENTS

| | | |
|---|---|---|
| 0332405 | 9/1989 | European Pat. Off. . |
| WO-A-8900589 | 1/1989 | World Int. Prop. O. . |

*Primary Examiner*—Thurman K. Page
*Assistant Examiner*—D. Gabrielle Phelan
*Attorney, Agent, or Firm*—Oblon, Spivak, McClelland, Maier & Neustadt

[57] ABSTRACT

Surgical adhesives, comprising an NCO-terminated hydrophilic urethane prepolymer derived from an organic polyisocyanate and a polyol component comprising a polyester polyol derived from an electron-attracting group-containing dicarboxylic acid, such as 2-ketoglutaric acid, are capable of being easily hydrolyzed within a living body after a certain period of time.

19 Claims, No Drawings

SURGICAL ADHESIVE

BACKGROUND OF THE INVENTION

1. Field of the Invention:

This invention relates to surgical adhesive.

2. Description of the Prior Art:

Matsuda et al. U.S. Pat. Nos. 4,740,534 and 4,994,542 disclose surgical adhesives, comprising NCO-terminated hydrophilic urethane prepolymers derived from organic polyisocyanates and hydrophilic polyether polyols. U.S. Pat. No. 4,804,691 discloses surgical adhesives, comprising NCO-terminated urethane prepolymers derived from aromatic polyisocyanates and polyester polyols obtained by ring-opening polymerization of epsilon-caprolactone or lactide.

Such adhesives, however, have some problem that the resulting polymers formed by curing of prepolymers remain without decomposed within living bodies for a long time after recovery of the operated parts.

SUMMARY OF THE INVENTION

It is an object of the present invention to provide a surgical adhesive capable of easily decomposed within living bodies after recovery of the operated parts.

It is another object of this invention to provide an adhesive for surgery having improved curability.

It is still another object of the invention to provide a surgical adhesive of lower toxicity to tissues.

Briefly, these and other objects of the present invention as hereinafter will become more readily apparent have been attained broadly by a surgical adhesive, which comprises at least one NCO-terminated hydrophilic urethane prepolymer, derived from (a) an organic polyisocyanate and (b) a polyol component comprising at least one polyester polyol derived from a dicarboxylic acid represented by the general formula:

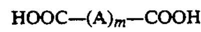

$$HOOC—(A)_m—COOH \quad (1)$$

wherein m is 0 or 1, A is $—CH_2—$ or an electron attracting group represented by the formula: —R—CO— or

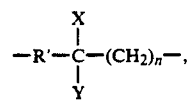

$$—R'—\underset{Y}{\overset{X}{C}}—(CH_2)_n—,$$

R is a divalent hydrocarbon group containing 1–8 carbon atoms, R' is a divalent hydrocarbon group or halogen-substituted hydrocarbon group containing 1–20 carbon atoms, X is a halogen atom or nitro or cyano group, Y is hydrogen atom, a halogen atom or nitro or cyano group, n is 0, 1 or 2.

DETAILED DESCRIPTION OF THE PREFERRED EMBODIMENTS

Polyol component

Suitable divalent hydrocarbon groups R include ones containing 1–8 carbon atoms (preferably 1–6 carbon atoms), for example, alkylene groups, such as methylene, ethylene, propylene, butylene, hexylene and octylene groups; alkenylene groups, such as ethenylene, propenylene and butenylene groups; alkynylene groups, such as acethylenylene groups; cycloalkylene groups, such as cyclohexylene group; arylene groups, such as phenylene and tolylene groups. Among these, preferred are alkylene groups, such as methylene and ethyleue groups.

Suitable divalent hydrocarbon groups R' include ones containing 1–20 carbon atoms (preferably 1–6 carbon atoms), for example, the same ones as R mentioned above, and divalent $C_{9-20}$ hydrocarbon groups, such as decylene, dodecylene, tridecylene and octadecylene groups; as well as these divalent hydrocarbon groups substituted with one or more halogen atoms (such as fluorine, chlorine and/or bromine), for example, fluoro-substituted alkylene groups such as $—(CH_2)_{n'}—(CF_2)_{m'}—$ (wherein n' is 0, 1 or 2, and m' is an integer of at least 1). Among these, preferred are alkylene groups, such as methylene and ethylene groups. Examples of halogen atoms of X and Y are fluorine, chlorine and bromine atoms. Preferable substituents X and Y are halogen atoms, particularly fluorine atoms. n is an integer of 0, 1 or 2, preferably 0 or 1.

Illustrative of suitable dicarboxylic acids represented by the general formula (1) are oxalic acid and malonic acid; alpha-keto-carboxylic acids, such as oxaloacetic acid, 2-ketoglutaric acid and alpha-keto-adipic acid; fluorine-containing dicarboxylic acids represented by the formula: $HOOC—(CH_2)_{n'}—(CF_2)_{m'}—(CH_2)_{n'}—COOH$ (wherein n' is 0, 1 or 2 and m' is an integer of at least 1, preferably 1–8); and the like. Among these dicarboxylic acids, preferred are alpha-keto-carboxylic acids, particularly 2-ketoglutaric acid.

In producing polyester polyols, used for preparation of prepolymers in this invention, said dicarboxylic acid of the formula (1) may be used in conjunction with one or more other carboxylic acids. Suitable other carboxylic acids include dicarboxylic acids, for example, aliphatic or aromatic dicarboxylic acids (such as glutaric, adipic, pimelic, suberic, azelaic, sebacic, fumaric, maleic, phthalic and terephthalic acids), and ester-forming derivatives thereof [anhydrides, lower alkyl esters (such as methyl, ethyl and propyl esters) and halides (such as chlorides)], for instance, maleic and phthalic anhydrides, dimethyl terephtharate and the like; and hydroxyl-containing carboxylic acids, for example, aliphatic or aromatic hydroxycarboxylic acids, such as glycolic, lactic, tartaric, malic and salicylic acids, and hydroxy-keto-carboxylic acids of the formula $HO—(CH_2)_n—CO—COOH$ (wherein n is an integer of at least 1), such as hydroxypyruvic acid, as well as ester-forming derivatives thereof, for instance, lactones, such as epsilon-caprolactone, and lactides, such as glycolide and lactide.

Polyester polyols can be produced by reacting the acid component comprising said dicarboxylic acid of the formula (1) and optionally one or more other carboxylic acids, or ester-forming derivatives thereof, with alcohol component comprising one or more polyols and/or alkylene oxides. Suitable polyols include low molecular weight polyols, including aliphatic, cycloaliphatic and aromatic ones, for example, dihydric alcohols, such as ethylene glycol, propylene glycol, 1,2-, 1,3- and 1,4-butane diols, 1,6-hexane diol, neopentyl glycol, diethylene glycol, cyclohexane diol, bis(hydroxymethyl)cyclohexane, bis(hydroxyethyl)benzene, hydrogenated bisphenol A and hydrogenated bisphenol F; trihydric alcohols, such as glycerol, trimethylolpropane, trimethyiolethane, 1,2,4-butane triol, and 1,2,6-hexane triol; polyhydric alcohols containing 4–8 or more hydroxyl groups, such as pentaerythritol, diglycerol, alpha-methyl-glucoside, sorbitol, xylitol, mannitol, glucose, fructose and sucrose; silanol-terminated polysiloxanes; high molecular weight polyols, for example, polyether polyols (such as those described below); and polyester polyols (those derived from these polyols and the above mentioned other carboxylic acids); as well as two or more of these polyols. Among these polyols, preferred are low molecular weight polyols (such as mono-, di- and tri-ethylene and propylene glycols, and 1,4-butane diol) and polyether polyols (particularly hydrophylic ones). Illustrative of suitable alkylene oxides (hereinafter referred to as AO) are ethylene oxide (hereinafter referred to as EO), propylene oxide (hereinafter referred to as PO), 1,2-, 2,3- and 1,4-butylene oxides, styrene oxide, and the like, as well as combinations of two or more of them, for example, combinations of EO with other AO (such as PO). Among these, preferred is EO.

In reacting the acid component with the alcohol component, the equivalent ratio of the alcohol component to the acid component may vary widely, such as 1-10 or more, preferably 1.5-4.

Reaction of the acid component with the alcohol component may be carried out by any known methods, for instance, 1) by dehydration polycondensation of a carboxylic acid with a polyol, 2) by addition of an AO to a carboxylic acid, 3) by dehydrohalogenation polycondensation of a carboxylic acid halide with a polyol, 4) by ester exchange reaction of a carboxylic acid lower ester with a polyol, 5) by ring-opening reaction of a lactone or a lactide, 6) by reaction of a carboxylic acid anhydride with an AO in the presence of a polyol, and so on.

Polyester polyols derived from said dicarboxylic acid of the formula (1) have an equivalent weight of usually 20-1000, preferably 50-500.

In producing prepolymers in this invention, polyester polyols derived from said dicarboxylic acid of the formula (1) may be used in conjunction with one or more other polyols, for example, low molecular weight polyols as mentioned above, and high molecular weight polyols, such as polyether polyols and other polyester polyols [those derived from these polyols (low molecular weight polyols and/or polyether polyols) and the above mentioned other carboxylic acids], as well as two or more of these polyols.

Suitable polyether polyols are adducts of one or more AOs (such as EO, PO, 1,2-, 2,3-, 1,3- and 1,4-butylene oxides, styrene oxide, epichlorohydrin and combinations of two or more of them) to one or more compounds containing at least two active hydrogen atoms, such as polyhydric alcohols, polyhydric phenols, amines, polycarboxylic acids, phosphoric acids and the like. Suitable examples of polyhydric alcohols include dihydric alcohols, such as ethylene glycol, propylene glycol, 1,3- and 1,4-butane diols, 1,6-hexane diol, neopentyl glycol, diethylene glycol, bis(hydroxymethyl)-cyclohexane, bis(hydroxyethyl)benzene, hydrogenated bisphenol A, hydrogenated bisphenol F, polytetramethylene glycols, polyester diols and silanol-terminated polysiloxanes; trihydric alcohols, such as glycerol, trimethylol propane, trimethylol ethane, 1,2,3-butane triol, 1,2,6-hexane triol and polyester triols; and polyhydric alcohols having 4-8 or more hydroxyl groups, such as pentaerythritol, diglycerol, alpha-methyl-glucoside, sorbitol, xylitol, mannitol, glucose, fructose, sucrose, and the like. Exemplary of suitable polyhydric phenols are mono- and poly-nuclear phenols, such as hydroquinone, catechol, resorcin, pyrogallol, and bisphenols (bisphenol A, bisphenol F, bisphenol B, bisphenol S and the like), as well as phenol-formaldehyde condensation products. Suitable amines are inclusive of ammonia; alkanol amines, such as mono-, di- and tri-ethanol amines, isopropanol amines and the like; aliphatic, aromatic, araliphatic and alicyclic monoamines, such as $C_1$-$C_{20}$ alkyl amines [methyl, ethyl, isopropyl, butyl, octyl and lauryl amines, and the like], aniline, toluidine, naphthyl amines, benzyl amine, cyclohexyl amine and the like, aliphatic, aromatic, alicyclic and araliphatic polyamines, such as $C_2$-$C_6$ alkylene diamines [ethylene diamine, hexamethylene diamine and the like], diethylene triamine, triethylene tetramine, tolylene diamines, phenylene diamines, xylylene diamines, diethyltolylene diamines, methylene dianilines, diphenylether diamines, isophorone diamine, cyclohexylene diamines, dicyclohexylmethane diamines and the like; and heterocyclic polyamines, such as piperazine, N-aminoethylpiperazine, and other heterocyclic polyamines, written in Japan Patent Publication No. 21044/1980. Illustrative of suitable polycarboxylic acids are those mentioned above, such as adipic and phthalic acids. Examples of phosphoric acids include ortho-, meta-, pyro- and polyphosphoric acids, phosphorous acid and acidic esters of these acids. Among these active hydrogen atom-containing compounds, preferred are polyhydric alcohols, particularly dihydric and trihydric alcohols (such as ethylene glycol and propylene glycol). Among AOs, preferred are EO and combinations thereof with other AO (particularly PO). Addition of AO (EO or combination thereof with other AO) to active hydrogen atom-containing compounds can be carried out in the usual way, with or without catalysts [such as alkaline catalysts, amine catalysts and acidic catalysts], under normal or an elevated pressure, in a single step or multistages. Addition of EO and other AO may be performed by random-addition, block-addition or combination of them (for instance random-addition followed by block-addition). Preferred is random-addition.

Polyether polyols have an equivalent weight (molecular weight per hydroxyl group) of usually 100-5,000, preferably 200-3,000. Polyether polyols having equivalent weight higher than 5,000 are too viscous to be used as surgical adhesives; while equivalent weight less than 100 results in lack of flexibility required for surgical adhesives.

It is preferred to use one or more hydrophilic polyether polyols in combination with said polyester polyol derived from said dicarboxylic acid of the formula (1), or/and in producing said polyester polyol as at least a part of the polyol component therefor. Oxyethylene content of such hydrophilic polyether polyols is usually at least 30%, preferably 50-90% by weight. Polyether polyols of oxyethylene content less than 30% by weight, having insufficient hydrophilic nature, have poor reactivity with body fluids resulting in reduced cure rate and poor bonding power with water-rich tissue and provide cured products of poor decomposibility.

Illustrative examples of polyester polyols are condensation products of dihydric and/or trihydric alcohols (ethylene glycol, propylene glycol, 1,3-and 1,4-butane diols, 1,6-hexane diol, neopentyl glycol, diethylene glycol, glycerol, trimethylolpropane and the like) and/or polyether polyols (such as those described above) with dicarboxylic acids (aliphatic or aromatic dicarboxylic acids, such as glutaric, adipic, sebacic, fumaric, maleic, phthalic and terephthalic acids) or ester-forming derivatives thereof (anhydrides and lower alkyl esters, such as maleic and phthalic anhydrides, dimethyl terephtharate, and the like); ring-opening polymerization products of lactones [such as epsilon-caprolactone].

Among these polyols, polyether polyols are preferred to polyester polyols.

In general, the polyol component (b), used for producing NCO-terminated urethane prepolymers, comprises at least 10%, preferably at least 20% of said polyester polyols derived from said dicarboxylic acid of the formula (1), 0–90% of other high molecular weight polyols (polyether polyols and/or other polyester polyols), and 0–20%, preferably 0–10% of low molecular weight polyols, based on the total weight of polyols. In case of polyester polyols derived from said dicarboxylic acid of the formula (1) free from oxyethylene groups, the amount of said polyester polyols is usually 10–70%, preferably 20–50%, and hydrophilic polyether polyols are used in an amount of generally 30–90%, preferably 50–80%. The polyol component (b) have an oxyethylene content (average) of usually at least 30%, preferably 50–90% by weight, an equivalent weight (average) of usually 100–5,000, preferably 200–3,000, and usually 2–8 hydroxyl groups, preferably 2–4 hydroxyl groups. Among these polyols, polyether polyols are preferred to polyester polyols.

Organic polyisocyanate

Organic polyisocyanates used for producing NCO-terminated hydrophilic urethane prepolymers, used in the surgical adhesive according to the present invention, include fluorine-containing ones and fluorine-free ones, and combinations of them.

Suitable F (fluorine)-containing polyisocyanates include, F-containing aliphatic polyisocyanates, and F-containing cycloaliphatic polyisocyanates, and mixtures of two or more of them.

Suitable F-containing aliphatic polyisocyanates include, for example, F-containing diisocyanates, represented by the formulae (2) and (3):

$$OCN—Rf—NCO \quad (2)$$

and $$OCN—CH_2—Rf—CH_2—NCO \quad (3)$$

In the formulae (2) and (3), Rf is a perfluoroalkylene group containing usually 1 to 20, preferably 1 to 10 carbon atoms, and 0 to 10, preferably 0 to 4 ether linkages. Specifically, there may be mentioned $—(CF_2)_k—$, $—CF_2CF_2OCF_2CF_2—$, $—CF_2CF_2O(CF_2)_{k'}OCF_2CF_2—$, $—CF(CF_3)O(CF_2)_{k'}OCF(CF_3)—$, and $—CF_2CF_2OCF_2CF(CF_3)O(CF_2)_{k'}OCF(CF_3)CF_2OCF_2CF_2—$, wherein k is 1 to 20, preferably 1 to 10, k' is 1 to 5, preferably 1 to 2. Among these, preferred are $—(CF_2)_k—$. F-containing polyisocyanates can be produced according to the methods described in J. Macromol. Sci.-Phys., B1, 831('67) and JPN Lay-open Patent No. 108055/1982.

Illustrative examples of F-containing cycloaliphatic polyisocyanates are fluorinated cycloaliphatic polyisocyanates, containing 4–15 carbon atoms (except those in NCO groups), such as F-containing isophorone diisocyanates, fluorinated hydrogenated xylylene diisocyanates, fluorinated hydrogenated 4,4'-diphenylmethane diisocyanates and fluorinated trans-cyclohexane-1,4-diisocyanates.

Among these polyisocyanates, preferred are F-containing aliphatic polyisocyanates, particularly F-containing diisocyanates of the fomula (3). The most preferred is 2,2,3,3,4,4,5,5-octafluorohexamethylene diisocyanate (hereinafter referred to as FHDI).

Suitable examples of fluorine-free polyisocyanates include aromatic polyisocyanates containing 6–20 carbon atoms [except carbon atoms in NCO groups], such as o-, m-and p-phenylene diisocyanates [hereinafter referred to as PDI], 2,4- and 2,6-tolylene diisocyanates [TDI], diphenylmethane-2,4'-and 4,4'-diisocyanates [MDI], naphthalene-1,5-diisocyanate, triphenylmethane-4,4',4"-triisocyanate, polymethylene polyphenylenepolyisocyanates [PAPI] obtained by phosgenation of aniline-formldehyde condensation products, m- and p-isocyanato-phenyl sulfonyl isocyanate, and the like; aliphatic polyisocyanates containing 2–18 carbon atoms, such as ethylenediisocyanate, tetramethylenediisocyanate, hexamethylenediisocyanate (hereinafter referred to as HDI), dodecamethylenediisocyanate, 1,6,11-undecane diisocyanate, 2,2,4-trimethylhexanediisocyanate, lysine ester diisocyanate, lysine ester triisocyanate, 2,6-diisocyanato-methyl caproate, bis(2-isocyanatoethyl fumarate, bis(2-isocyanatoethyl) carbonate, 2-isocyanatoethyl-2,6-diisocyanato hexanoate, and the like; alicyclic polyisocyanates containing 4–15 carbon atoms, such as isophorone diisocyanate, dicyclohexylmethane diisocyanates, cyclohexylene diisocyanates, methylcyclohexylene diisocyanates, bis(2-isocyanato-ethyl) 4-cyclohexene-1,2-dicarboxylate, and the like; araliphatic polyisocyanates containing 8–15 carbon atoms, such as xylylene diisocyanates, diethylbenzene diisocyanates, and the like; and modified polyisocyanates of these polyisocyanates, containing urethane, carbodiimide, allophanate, urea, biuret, urethdione, urethimine, isocyanurate and/or oxazolidone groups, such as urethane-modified TDI, carbodiimide-modified MDI, urethane-modified MDI, and the like; as well as mixtures of two or more of them. Among these fluorine-free polyisocyanates, preferred are aromatic polyisocyanates (preferably diisocyanates), particularly PDI, TDI (including 2,4- and 2,6-isomers, mixtures of them and crude TDI), MDI (including 4,4'- and 2,4'-isomers, mixtures of them and crude MDI or PAPI), and modified polyisocyanates containing urethane, carbodiimide, allophanate, urea, biuret and/or isocyanurate groups, derived from PDI, TDI and/or MDI. The most preferred is p-PDI, with respect to low toxicity.

Among these organic polyisocyanates, preferred are F-containing polyisocyanates, and combinations thereof with 50% or less, particularly 20% or less of F-free polyisocyanates, based on the total weight of the polyisocyanates.

Prepolymer

In reacting at least one polyisocyanate (a) with the polyol component (b) comprising said polyester polyol derived from a dicarboxylic acid of the general formula (1) to form NCO-terminated hydrophlic urethane prepolymers, ratio of NCO/OH is generally 1.5 or more, preferably 1.6–5, more preferably 1.7–3.

The reaction of (a) with (b) forming prepolymers can be performed in the usual manner, under the usual conditions (for example, at a temperature between 50° C. and 100° C.) The reaction may be carried out in the presence of a catalyst. Prepolymers may be prepared in any order, for instance, 1) by reacting (a) with (b); 2) by reacting (a) with a part of (b) [for example, either said polyester polyol or a polyether polyol and/or low molecular weight polyol], followed by reacting the resulting intermediate prepolymer with the rest of (b) [for example, either a polyether polyol and/or low molecular weight polyol or said polyester polyol]; or 3) by blending a prepolymer of said polyester polyol with a prepolymer of a polyether polyol and/or low molecular weight polyol. Among these, preferred is 1). In case where two or more polyisocyanates (for instance, F-containing one and F-free one) are used in conjunction, these polyisocyanates may be reacted in any order similarly. It is preferred to react F-free polyisocyanates at early stages of prepolymer production so as to provide F-containing polyisocyanate terminated prepolymers.

NCO-contents of NCO-terminated hydrophilic prepolymers are usually 1-10%, preferably 2-8% by weight. Prepolymers of NCO-content less than 1% by weight are of poor reactivity and bring about reduction of cure rate and insufficient bonding power to tissues. Higher NCO-content than 10% by weight results in brittle cured resins of poor flexibility which are not deformable following the movement of living organism.

Adhesives of the present invention may contain, if necessary, physiologically active materials [such as agents affecting central nervous system, antiallergic agents, cardiovascular agents, agents affecting respiratory organs, agents affecting digestive organs, hormone preparations, agents affecting metabolism, antitumor agents, antibiotic preparations, chemotherapeutics, antimicrobias, local anesthetics, antihistaminics, antiphlogistics, astringents, vitamins, antifungal agents, peripheral nervous anesthetics, vasodilators, crude drug essences, tinctures, crude drug powders, hypotensive agents, and the like], fillers [for example, carbon black, metal oxides, such as red iron oxide and titanium dioxide, silicates, such as calcium silicates and sodium silicates, acrylic resin powders, various ceramic powders, and the like]; softening agents [such as DBP(dibutylphosphate), DOP(dioctylphosphate), TCP(tricresylphosphate), tributoxyethylphosphates, and other esters of various types]; stabilizers, such as trimethyldihydroquinone, phenyl-beta-naphthyl amine, p-isopropoxydiphenylamine, diphenyl-p-phenylene diamine, and the like. These additives may be used in an amounts of usually 0-20%, preferably 0-5%, based on the weight of the adhesive according to this invention.

NCO-terminated prepolymers can bring about rapid polymerization in the presence of trace amounts of water such as moisture in air and result in forming tough membrane. Accordingly, it is necessary to use dehydrated ones as these main components and also other compounding additives, and it is preferred to shut off air during production of adhesives. Adhesives, thus obtained, can be stored for a long period of time within airtight vessels, such as ampule.

Application of Surgical Adhesive

In applying adhesives of the present invention in surgery, suitable application methods include those by using brushes, tweezers, applicators, specially-designed spatula or syringes, or the like; and those involving spray coating using inner gases, such as Freons, nitrogen or the like. Bonding of tissues can be achieved, for example, by direct coating techniques, simply applying the adhesive to the tissues; by cover-coating techniques, using, as an aid for hemostasis or anastomosis, thin sheets or meshes made of polyesters (such as Dacron), oxidized celllose, collagen, polyurethanes or the like, cotton-like materials, or fragments of tissues, such as veins, musculation or mascular membrane or the like [wherein these materials are applied onto the affected parts followed by coating thereon the adhesives]; or by sealing techniques for sutured parts, wherein sutures are partly applied followed by applying the adhesive to seal the remaining conjugation parts. Adhesives of the present invention can be used, not only for tissure adhesion, but also as coating, embolus or sealing materials in cardiovascular surgery via direct coating or injection by catheters. Adhesives of this invention may be applied in the form of adhesive sheet or with use of surgical instruments, as described in EP Appln. No 90 303 222.5.

Applicable tissues include, for example, vascular vessels, heart, lung, windpipe, esophagus, stomach, kidney, duoderm, small intestine, large intestine, rectum, liver, pancreas, spleen, nerve, skin and the like.

Surgical adhesives according to this invention, comprising NCO-terminated hydrophilic urethane prepolymer derived from (a) an organic polyisocyanate and (b) a polyol component comprising a polyester polyol derived from a dicarboxylic acid of the formula (1), are capable of being decomposed within living bodies, within several weeks in case of easily decomposable ones, and within several months in case of slowly decomposable ones. Thus, adhesives of the invention can be applied to living bodies in safety, as they are decomposed out, without remaining the resulting polymers for a long time, within a certain period of time, after recovery of the operated parts.

In addition to decomposibility, surgical adhesives of the present invention also have sufficiently high cure rate, sufficient bonding power for tissues and flexibility capable of being deformed in accordance with movement of tissues.

Particularly, adhesives of the present invention, comprising a prepolymer prepared by reacting (a) with (b) at NCO/OH ratio of higher than 1.5 can provide improved curability and improved bonding power to tissue.

Besides, adhesives of this invention, comprising a prepolymer prepared using a F-containing polyisocyanate as (a), are of lower toxicity to tissues and cause no or little toxicological problem.

Accordingly, adhesives of the present invention have effects of considerably improving safety and security in medical treatments, including surgical operations. There can be attained remarkable improvements in medical technology, such as shortening of operation time, hemostasis, prevention of leaking emzyme from viscera or the like, prevention of minute blood bessel occusion, and nerve anastomosis, as well as provisional fixing before suturing, and ensuring of bonding by combination of adhesion with suturing. Furthermore, the invention can provide high reliance and high efficiency, not only in operation, but also in medical treatment at large, for example, joining of incised wound or culting portions, adhesive treatment in dental surgery, curative means by controled release of drugs in combination with physiologically active materials, and so on.

Having generally described the invention, a more complete understanding can be obtained by reference to certain specific examples, which are included for purposes of illustration only and are not intended to be limiting unless otherwise specified.

In the following Examples, parts and % represent parts by weight and % by weight, respectively. In the following, PEO represents polyethyleneoxide, PPO represents polypropyleneoxide, PEG represents polyetheleneglycol, and PPG represents polypropyleneglycol.

PREPARATION EXAMPLE 1

Preparation of Polyol A-1

A mixture of 2- ketoglutaric acid (1 mole), diethylene glycol (3 moles) and anhydrous aluminum chloride (0.001 mole) was stirred, and dehydration condensation reaction was carried out under heating at 90° C., for 3 hours, then at 130° C. for 2 hours, and finally at 150° C. for 2 hours. The reaction product was purified by dissolving it in chloroform, followed by liquid separation treatment (twice with water, then with an aqueous solution of sodium hydrogen carbonate and finally with a saturated aqueous solution of sodium chloride) and then removing chloroform to obtain a polyester polyol (Polyol A-1).

PREPARATION EXAMPLE 2

Preparation of Polyol A-2

A reaction product of 1,4-butane diol (3 moles) with metallic sodium was mixed into tetrahydrofuran solvent under stirring, and malonic dichloride (1 mole) was added thereto dropwise. From the reaction product, inorganic salt was filtered off and the solvent was removed to obtain a polyester polyol (Polyol A-2).

PREPARATION EXAMPLE 3

Preparation of Polyol A-3

A mixture of HOOC—$(CF_2)_4$ —COOH (1 mole), tripropylene glycol (3 moles) and anhydrous aluminum chloride (0.001 mole) was stirred, and dehydration condensation reaction was carried out in the same manner as in Preparation Example 1 to obtain a polyester polyol (Polyol A-3).

PREPARATION EXAMPLE 4

Preparation of Polyol A-4

To a mixture of oxalic acid (1 mole) with lithium hexafluorophosphate (0.01 mole), ethylene oxide (1 mole) was added little by little and reacted at 120° C. After completion of reaction, the resulting product was neutralized and purified to obtain a polyester polyol (Polyol A-4).

EXAMPLE 1

A mixture of 90 parts of a polyether polyol (PEO-PPO random copolymer, having an average molecular weight of 3000 and an oxyethylene content of 80%) with 10 parts of Polyol A-1 was dehydrated under reduced pressure, and then FHDI was added thereto in such an amount providing NCO/OH ratio 2/1 and reacted at a temperature of 80° C. for 8 hours to obtain an NCO-terminated urethane prepolymer, which is Surgical Adhesive I of the present invention.

EXAMPLE 2

A mixture of 80 parts of a polyether polyol (PEO-PPO random copolymer, having an average molecular weight of 4000 and an oxyethylene content of 60%) with 20 parts of Polyol A-2 was dehydrated under reduced pressure, and then p--PDI was added thereto in such an amount providing NCO/OH ratio of 2/1 and reacted at a temperature of 80° C. for 8 hours to obtain an NCO-terminated urethane prepolymer, which is Surgical Adhesive II of the present invention.

EXAMPLE 3

A mixture of 50 parts of a PEG having an average molecular weight of 1000 with 50 parts of Polyol A-3 was dehydrated under reduced pressure, and then TDI was added thereto in such an amount providing NCO-/OH ratio of 2/1 and reacted at a temperature of 80° C. for 8 hours to obtain an NCO-terminated urethane prepolymer, which is Surgical Adhesive III of the present invention.

EXAMPLE 4

A mixture of 50 parts of a PPG having an average molecular weight of 3000 with 50 parts of Polyol A-1 was dehydrated under reduced pressure, and then FHDI was added thereto in such an amount providing NCO/OH ratio of 2/1 and reacted at a temperature of 80° C. for 8 hours to obtain an NCO-terminated urethane prepolymer, which is Surgical Adhesive IV of the present invention.

EXAMPLE 5

Polyol A-4 was dehydrated under reduced pressure, and then TDI was added thereto in such an amount providing NCO/OH ratio of 2/1 and reacted at a temperature of 80° C. for 8 hours to obtain an NCO-terminated urethane prepolymer, which is Surgical Adhesive V of the present invention.

COMPARATIVE EXAMPLE 1

A mixture of 90 parts of a polyether polyol (PEO-PPO random copolymer, having an average molecular weight of 3000 and an oxyethylene content of 80%) with 10 parts of a PPG having an average molecular weight of 200 was dehydrated under reduced pressure, and then FHDI was added thereto in such an amount providing NCO/OH ratio of 2/1 and reacted at a temperature of 80° C. for 8 hours to obtain an NCO-terminated urethane prepolymer, which is Surgical Adhesive VI for comparison.

COMPARATIVE EXAMPLE 2

A mixture of 90 parts of a polyether polyol (PEO-PPO random copolymer, having an average molecular weight of 3000 and an oxyethylene content of 80%) with 10 parts of a polycaprolactone polyol having an average molecular weight of 520 was dehydrated under reduced pressure, and then TDI was added thereto in such an amount providing NCO/OH ratio of 2/1 and reacted at a temperature of 80° C. for 8 hours to obtain an NCO-terminated urethane prepolymer, which is Surgical Adhesive VII for comparison. COMPARATIVE EXAMPLE 3

A polylactic acid having an average molecular weight of 2900 was dehydrated under reduced pressure, and then TDI was added thereto in such an amount providing NCO/OH ratio of 2/1 and reacted at a temperature of 80° C. for 8 hours to obtain an NCO-terminated urethane prepolymer, which is Surgical Adhesive VIII for comparison.

TESTING EXAMPLE 1

Adhesion Properties Test in vivo

Each of Surgical Adhesive I to VIII was coated onto a fluorine-containing resin film to form a surgical adhesive sheet.

Liver of a dog was cramped with forceps in accordance with an immaginal cutting line of about 2 cm length, and cut along with the inside of the forceps. To all over this section, each surgical adhesive sheet was pressed; and, after 10 minutes, the fluorine resin sheet was removed therefrom and the adhesive was transferred to the affected part.

Surgical Adhesives I to VII attained complete sealing and hemostasis, without any dificulties in treating and in hemostasis; while Surgical Adhesive VIII of Comparative Example 3 was highly crystalline and waxy and had dificulties in treating and in hemostasis.

TESTING EXAMPLE 2

Decomposibility Test in vitro

Methanol was added to each of Surgical Adhesives I to VIII and reacted therewith at 50° C. for 48 hours to block the terminal NCO groups of the prepolymer with methanol. To each methanol-blocked prepolymer, was added a phosphate buffer (pH=6.8), and decomposibility at 37° C. was determined by measuring molecular weight distribution with gel permeation chromatography (GPC) after 3 days and after 10 days. The results were as follows:

Surgical Adhesives I, II and IV: decomposition was observed with GPC after 10 days. (It was confirmed by NMR that the decomposition was occured in the polyester polyol portion.)

Surgical Adhesives III and V: polyester polyol portion was decomposed completely after 3 days.

Surgical Adhesives VI, VII and VIII: no decomposition was observed after 10 days.

TESTING EXAMPLE 3

Decomposibility Test in vivo

Each of Surgical Adhesives I to VIII was coated in a small amount onto surface of liver of a mouse to seal the affected part. After 3 months, each mouse was anatomized and decomposibility was examined.

It was observed that Surgical Adhesives I, II and IV were decomposed considerably and lost adhesion power with the tissue, though the original shape was maintained, and decomposition proceeded in part. As to Surgical Adhesives III and V, more considerable decomposition was observed, as compared the above three. On the other hand, substantially no decomposition was observed in Surgical Adhesives VI and VII. Surgical Adhesive VIII was waxy and could not be put to the test.

What is claimed as new and desired to be secured by Letters Patent is:

1. A surgical adhesive which comprises at least one NCO-terminated hydrophilic urethane prepolymer, derived from (a) an organic polyisocyanate and (b) a polyol component comprising at least one polyester polyol derived from a dicarboxylic acid represented by the general formula:

$$HOOC—(A)_m—COOH \quad (1)$$

wherein m is 0 or 1, A is $—CH_2—$ or an electron attracting group represented by the formula: —R—CO— or

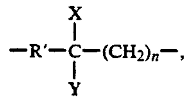

R is a divalent hydrocarbon group containing 1-8 carbon atoms, R' is a divalent hydrocarbon group or halogen-substituted hydrocarbon group containing 1-8 carbon atoms, X is a halogen atom or nitro or cyano group, Y is hydrogen atom, a halogen atom or nitro or cyano group, n is 0, 1 or 2, wherein the polyester polyols derived from a dicarboxylic acid have an equivalent weight of 20-1000, the ratio of NCO/OH is 1.5 or more, and the NCO content of the NCO-terminated hydrophilic urethane prepolymer is 1-10%.

2. The adhesive of claim 1, wherein said dicarboxylic acid is at least one dicarboxylic acid selected from the group consisting of oxalic acid, alpha-keto-carboxylic acids and fluorine-containing dicarboxylic acids of the formula: $HOOC—(CH_2)_{n'}(CF_2)_{m'}—(CH_2)_{n'}—COOH$ wherein n' is 0, 1 or 2 and m' is an integer of at least 1.

3. The adhesive of claim 1, wherein said dicarboxylic acid comprises 2-ketoglutaric acid.

4. The adhesive of claim 1, wherein said polyol component further comprises a hydrophilic polyether polyol.

5. The adhesive of claim 4, wherein said polyol component comprises 10-90% by weight of said polyester polyol and 10-90% by weight of said hydrophilic polyether polyol.

6. The adhesive of claim 4, wherein said hydrophilic polyether polyol contains oxyethylene groups.

7. The adhesive of claim 4, wherein said hydrophilic polyether polyol is a polyoxyethylene diol or a polyoxyethylene/oxypropylene diol.

8. The adhesive of claim 1, wherein said polyester polyol contains oxyethylene groups.

9. The adhesive of claim 1, wherein said polyol component has an oxyethylene content of 30-90% by weight.

10. The adhesive of claim 1, wherein said polyol component has an equivalent weight of 200-3000.

11. The adhesive of claim 1, wherein said polyisocyanate comprises a fluorine-containing polyisocyanate.

12. The adhesive of claim 11, wherein said fluorine-containing polyisocyanate is at least one polyisocyanate selected from the group consisting of fluorine-containing diisocyanates of the formula (2) or (3):

$$OCN—Rf—NCO \quad (2)$$

$$OCN—CH_2—Rf—CH_2—NCO \quad (3)$$

wherein Rf is a perfluoroalkylene group containing 1 to 20 carbon atoms and 0 to 10 ether linkages.

13. The adhesive of claim 1, wherein said prepolymer is obtained by reacting said polyisocyanate with said polyol component in such an amount providing NCO/OH ratio of 1.6-5.

14. The adhesive of claim 1, wherein said prepolymer has an NCO-content of 2-8% by weight.

15. The adhesive of claim 1, which contains up to 20% by weight of at least one additive selected from the group consisting of carbon black, metal oxides, silicates, acrylic resin powders, ceramic powders, softening agents, stabilizers and physiologically active mateials.

16. The adhesive of claim 15, wherein the physiologically active material is selected from the group consisting of agents affecting central nervous system, antiallergic agents, cardiovascular agents, agents affecting respiratory organs, agents affecting digestive organs, hormone preparations, agents affecting metabolism, antitumor agents, antibiotic preparations, chemotherapeutics, antimicrobias, local anesthetics, antihistaminics, antiphlogistics, astringents, vitamins, antifungal agents, peripheral nervous anesthetics, vasodilators, and hypotensive agents.

17. A method for surgical bonding of tissue, which comprises applying the surgical adhesive of claim 1.

18. The method of claim 17, wherein said tissue is vascular vessel, heart, lung, windpipe, esophagus, stomach, kidney, small intestine, large intestine, rectum, liver, pancreas, spleen, nerve or skin.

19. The adhesive of claim 15, wherein the physiologically active material is selected from the group consisting of crude drug essences, tinctures and crude drug powders.

* * * * *